United States Patent
Baker et al.

(10) Patent No.: US 11,202,806 B2
(45) Date of Patent: Dec. 21, 2021

(54) AMOEBA THERAPEUTIC DRESSINGS, BIOMATERIALS, AND SOLUTIONS

(71) Applicant: VISCUS BIOLOGICS, LLC, Cleveland, OH (US)

(72) Inventors: Justin J. Baker, Cleveland, OH (US); Peter H. Gingras, Cleveland, OH (US)

(73) Assignee: VISCUS BIOLOGICS, LLC, Cleveland, OH (US)

( * ) Notice: Subject to any disclaimer, the term of this patent is extended or adjusted under 35 U.S.C. 154(b) by 222 days.

(21) Appl. No.: 16/342,617

(22) PCT Filed: Oct. 18, 2017

(86) PCT No.: PCT/US2017/057158
§ 371 (c)(1),
(2) Date: Apr. 17, 2019

(87) PCT Pub. No.: WO2018/075626
PCT Pub. Date: Apr. 26, 2018

(65) Prior Publication Data
US 2019/0231827 A1    Aug. 1, 2019

Related U.S. Application Data

(60) Provisional application No. 62/409,406, filed on Oct. 18, 2016.

(51) Int. Cl.

| | | |
|---|---|---|
| *A61K 35/68* | (2006.01) | |
| *A61K 9/70* | (2006.01) | |
| *A61K 9/00* | (2006.01) | |
| *A61P 17/02* | (2006.01) | |
| *A61L 15/32* | (2006.01) | |
| *A61P 31/04* | (2006.01) | |
| *A01N 63/00* | (2020.01) | |
| *A61F 13/00* | (2006.01) | |
| *A61K 47/46* | (2006.01) | |

(52) U.S. Cl.
CPC .............. *A61K 35/68* (2013.01); *A01N 63/00* (2013.01); *A61F 13/00063* (2013.01); *A61K 9/0014* (2013.01); *A61K 9/7007* (2013.01); *A61K 47/46* (2013.01); *A61L 15/325* (2013.01); *A61P 17/02* (2018.01); *A61P 31/04* (2018.01)

(58) Field of Classification Search
CPC ....... A61K 35/68; A61K 47/46; A61L 15/325; A61P 17/02; A61P 31/04
See application file for complete search history.

(56) References Cited

U.S. PATENT DOCUMENTS

| | | |
|---|---|---|
| 8,168,167 B2 | 5/2012 | Bodennec et al. |
| 8,551,471 B2 | 10/2013 | Filutowicz et al. |
| 8,715,641 B2 | 5/2014 | Filutowicz et al. |
| 9,192,167 B2 | 11/2015 | Plasson et al. |
| 9,288,944 B2 | 3/2016 | Coppinger et al. |
| 2014/0056850 A1 | 2/2014 | Filutowicz et al. |
| 2014/0322167 A1 | 10/2014 | Plasson et al. |
| 2014/0328800 A1 | 11/2014 | Plasson et al. |

FOREIGN PATENT DOCUMENTS

| | | |
|---|---|---|
| FR | 2984081 A1 | 6/2013 |
| WO | 2008/043969 A2 | 4/2008 |

OTHER PUBLICATIONS

Amoeba: "Amoeba and Viscus Biologics announce a joint program for the treatment of multi-resistant bacteria for human wound care", Press Release, Jun. 27, 2017 (Jun. 27, 2017), XP002776757, http://www.amoeba-biocide.com/en/news/collaboration-wound-care-treatment.
PCT International Search Report and Written Opinion for corresponding International Application Serial No. PCT/US2017/057158, dated Jan. 12, 2018, pp. 1-64.

*Primary Examiner* — Ruth A Davis
(74) *Attorney, Agent, or Firm* — Tarolli, Sundheim, Covell & Tummino LLP (57) ABSTRACT

A method of treating or preventing a microbial infection in a subject is described. The method includes contacting a microorganism within the subject with a composition comprising one or more species of amoebae of the genus *Willaertia*. Antibiotic wound dressings and kits for providing amoeba for treatment or prevention of microbial infection in a subject are also described.

12 Claims, 3 Drawing Sheets

AMOEBA PHAGE™ DRESSING FORMATS

VIAL
AMOEBA CYSTS
COLLAGEN POWDER

GAUZE
ROLL OF COMBAT GAUZE EMBEDDED WITH AMOEBA CYSTS AND COLLAGEN POWDER

FOIL POUCH
FOIL POUCH OF COLLAGEN POWDER AND AMOEBA CYSTS

AMOEBA THERAPEUTIC DRESSINGS, BIOMATERIALS, AND SOLUTIONS

CONTINUING APPLICATION DATA

This application claims the benefit of U.S. Provisional Patent Application Ser. No. 62/409,406, filed Oct. 18, 2016, the entirety of which is hereby incorporated by reference for all purposes.

BACKGROUND

Antibiotic or antimicrobial resistance is a growing problem, and if left unaddressed, will cause millions of otherwise preventable deaths and cost millions of dollars. The problem is alarming since there is little economic incentive for companies to develop new antibiotics until bacteria have developed resistance to current antibiotics, which would also compete with the new antibiotic. Overuse of antibiotics has also contributed to bacteria developing resistance. As more and more bacterial infections become resistant to antibiotics, the risk of acquiring an infection that is untreatable by antibiotics (i.e., a multidrug resistant (MDR) infection) will continue to grow. Simple cuts and wounds can lead to life- or limb-threatening infections. Throughout the U.S., addressing antibiotic drug resistance is a top priority as each year antibiotic-resistant bacteria infect nearly two million people and more than 23,000 people die each year from those infections. Innovations that treat or prevent infection, and in particular kill MDR bacteria, while avoiding contributing to antibiotic resistance, are highly needed.

Chronic wounds are particularly susceptible to the development of infection. The growing elderly population, increasing incidence of diabetes, is also leading to an increase in chronic wounds. Wound healing can be dramatically adversely affected or prevented by wound infection, among others. To reduce the likelihood of wound infections, wound dressings have been proposed which contain a microbicidal substance. Currently, the standard antimicrobial dressings in the market are silver based dressings. For example, U.S. Pat. No. 6,468,521 describes a wound dressing using a hydrophilic polymer carrier impregnated with a silver-amine complex that provides an antibiotic effect. However, there are substantial disadvantages to the use of silver as an antimicrobial (e.g., silver is cytotoxic).

Another problem common to chronic wounds is the presence of a bacterial biofilm that resists treatment with typical antibiotics. Bowler et al., Clin Microbiol Rev, vol. 14, no. 2, pp. 244-269, 2001. MDR bacteria often form a protective biofilm which reduces the effectiveness of antibiotics. Studies have shown that from 60 to 90% of chronic wounds sampled were positive for bacteria and biofilm, and one claimed "it is likely that almost all chronic wounds have biofilm communities on at least part of the wound bed." Zhao et al., Adv Wound Care (New Rochelle), 2(7), p. 389-399 (2013). New treatments for chronic wounds including the ability to prevent or removing biofilm formation are being developed. Klueh et al., J Biomed Mater Res, vol. 53, no. 6, pp. 621-631, 2000; Hill et al., J Antimicrob Chemother, vol. 65, no. 6, pp. 1195-1206, 2010.

The US military has also begun focusing on treating wounded soldiers having antibiotic resistant bacteria. The U.S. military is effective in providing rapid, high quality health care for service members wounded in Iraq and Afghanistan; however, many of these personnel develop harmful, even fatal infections that can't be cured due to the presence of MDR bacteria. Within the military, clinical studies suggest that the source of these MDR bacterial infections is hospital-acquired infection (HAI) in both deployed hospitals and receiving medical centers. Antibiotics are often used prophylactically as the first line of response to combat wounds, and while this dramatically reduces the number of casualties due to infection, such overuse has contributed to the development of MDR. From 2002 to 2005, there was increased bacterial resistance to nearly all antibiotics tested at one military treatment facility in Iraq. *Acinetobacter baumanii* has been a common HAI in the military, and in fact is so common, especially among burn patients, that it was dubbed "Iraqibacter." Therefore, innovations to treat wounds infected by MDR resistant bacteria, while avoiding contributing to the development of antibiotic resistance, are a high priority to the medical community, and in particular the military medical community.

SUMMARY

In one aspect, the present invention provides a method of treating or preventing a microbial infection in a subject, comprising: contacting a microorganism within the subject with a composition comprising one or more species of amoebae of the genus *Willaertia*. In some embodiments, the amoebas are provided in a pharmaceutically acceptable carrier, which in further embodiments, the subject has a skin wound, and the amoebas are administered to the skin wound. In some embodiments, *Willaertia magna* species of amoebas are administered. Examples of microbial infection include bacterial infection, and in particular antibiotic-resistant bacterial infections.

In another aspect, the present invention provides a system comprising a composition including one or more species of amoeba of the genus *Willaertia*; and a medical device comprising said composition. In some embodiments, the medical device comprises an antibiotic wound dressing. The antibiotic wound dressing includes a backing having a first surface and a second surface opposite the first surface; a pharmaceutically acceptable support material applied to a portion of the first surface of the backing; and one or more amoebas of the genus *Willaertia* dispersed within the pharmaceutically acceptable support material.

In some embodiments, the antibiotic wound dressing further comprises an adhesive layer provided on at least a part of the first surface of the backing to secure the adhesive dressing to the skin and over the wound of a subject. In further embodiments, the backing is a transparent, water-impermeable polymer. In additional embodiments, the pharmaceutically acceptable support material comprises collagen, while in yet further embodiments the *Willaertia* amoeba are included in cyst form.

In another aspect, the present invention provides a wound treatment kit. The kit includes a therapeutically effective amount of amoebas of the genus *Willaertia* in a pharmaceutically acceptable carrier; and a package for holding the pharmaceutically acceptable carrier including the amoebas. In some embodiments, the amoebas are of the *Willaertia magna* species, while in additional embodiments the amoebas are in the cyst form. The kits can also include a wound dressing material, and in come embodiments the pharmaceutically acceptable carrier comprises collagen such as collagen powder.

The present invention also provides a wound dressing that eliminates MDR bacteria while promoting healing. The wound dressing is composed of a collagen component with anti-inflammatory properties that attracts fibroblasts, reduces harmful enzymes, and speeds healing of chronic wounds. In addition, dormant *Willaertia* amoebae are included in the dressing, waiting for moisture to rehydrate the dressing and for bacteria to appear. When applied to a moist wound environment, the lyophilized amoeba cysts rehydrate, sprout, and actively seek out pathogenic bacteria including dormant persister cells, biofilm enmeshed bacteria, and those that are resistant to antibiotics. The amoebae subsequently phagocytize and internally digest the bacteria, their natural prey, thereby preventing endotoxic shock due to widespread bacterial death and subsequent lysis common with antibiotic use.

An advantage of using *Willaertia* amoebae for the treatment for infected wounds is that it allows cost savings by reducing the requirement for systemic antibiotic administration. This will also be attractive for policy makers as the strategy for combating antibiotic resistant bacteria also involves decreased use of antibiotics, especially long-term use of antibiotics as this gives bacteria the opportunity to develop resistance. A Swedish audit found that 26.6% of chronic wound patients were receiving antibiotic treatment and that an additional 33.5% were not currently on antibiotics but had been receiving antibiotics within the previous 6 months. Howell-Jones et al., Journal of Antimicrobial Chemotherapy, vol. 55, pp. 143-149, 2005.

BRIEF DESCRIPTION OF THE DRAWINGS

The foregoing and other features of the present application will become apparent to those skilled in the art to which the present application relates upon reading the following description with reference to the accompanying drawings, in which.

DETAILED DESCRIPTION

The present invention provides a method of treating or preventing microbial infection in a subject. The method includes contacting a microorganism within the subject with a composition comprising one or more species of amoebae of the genus *Willaertia*. In particular, the method provides a method of treating or preventing infection of a skin wound. The invention also includes antibiotic wound dressings and kits for providing amoebae for treatment or prevention of microbial infection in a subject.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

Treat", "treating", and "treatment", etc., as used herein, refer to any action providing a benefit to a patient at risk for or afflicted with an infection, including improvement in the condition through lessening or suppression of at least one symptom, delay in progression of the infection, etc.

As used herein, the term "prevention" includes either preventing the onset of a clinically evident infection altogether or preventing the onset of a preclinically evident stage of infection in individuals at risk, such as individuals having a skin wound. Also intended to be encompassed by this definition is the prevention of the development of infection or to arrest or reverse the progression of infection. This includes prophylactic treatment of those having an enhanced risk of developing an infection. An elevated risk represents an above-average risk that a subject will develop an infection, which can be determined, for example, through presence of a skin wound, family history, immunosuppression, or exposure to infection.

As used herein, the term "microorganism" refers to any species or type of microorganism, including but not limited to, bacteria, archea, fungi, protozoans, *mycoplasma*, and parasitic organisms. The present invention contemplates that a number of microorganisms encompassed therein will also be pathogenic to a subject.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc. Also included within this term are prokaryotic organisms that are gram negative or gram positive. In some embodiments, the bacteria are those capable of causing disease (pathogens) and those that cause production of a toxic product, tissue degradation or spoilage.

As used herein, the term "fungi" is used in reference to eukaryotic organisms such as the molds and yeasts, including dimorphic fungi.

As used herein the term "biofilm" refers to an aggregation of microorganisms (e.g., bacteria) surrounded by an extracellular matrix or slime adherent on a surface in vivo or ex vivo, wherein the microorganisms adopt altered metabolic states.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts (e.g., monomeric or oligomeric subunits or other byproducts) at toxic concentrations, does not cause prolonged inflammation or irritation, or does not induce more than a basal immune reaction in the host.

All scientific and technical terms used in the present application have meanings commonly used in the art unless otherwise specified. The definitions provided herein are to facilitate understanding of certain terms used frequently herein and are not meant to limit the scope of the present application.

Treatment of Microbial Infection

In one aspect, the present invention provides a method of treating or preventing a microbial infection in a subject. The method includes contacting a microorganism within the subject with a composition comprising one or more species of amoebae of the genus *Willaertia*. Within the subject, as used herein, includes microorganisms on the surface (e.g., skin, mucous membrane) of the subject, as well as microorganisms within a skin wound of the subject. Amoebae such as *Willaertia* amoebae possess the ability to consume wound bacteria, especially pathogens that are resistant to chemical antibiotics. As a result, they can be used as an effective prophylactic, an adjunct to current therapies, or an independent remedy. In some embodiments, amoebae (or their cysts) are applied to infected tissue where they quickly reduce the microbial load and, in doing so, promote healing. In some embodiments, two or more compatible species are utilized in a composition. Such combinations are contemplated to find particular use in the killing of drug resistant microorganisms and mixed populations of microorganisms.

Figure 1:
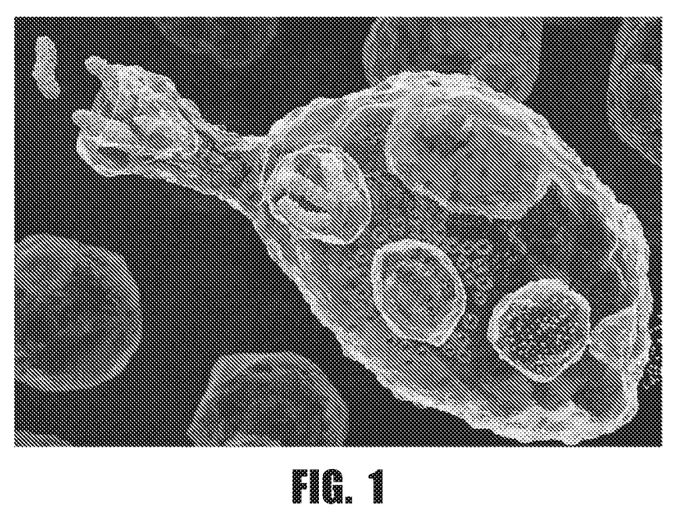
FIG. 1 provides an image showing phagocytosis of bacteria, the process by which *Willaertia magna* eliminates bacteria.

*Willaertia* is an amoeboid genus of Heterolobosea. See Panek T. and Cepicka I., "Diversity of Heteroblosea", Genetic Diversity in Microorganisms, M. Caliskan, ed., Chapter 1, Intech Publishing, 2012. FIG. 1 provides an image showing phagocytosis of bacteria by a *Willaertia* amoeba. *Willaertia* amoebae have a life cycle in which the amoeba can exist as a cyst, an amoeboid, or a flagellate, with *Willaertia* amoebae having four flagella. Although the morphology of *Willaertia* resembles that of the Vahlkamphiidae family, with its eruptive pseudopods in its vegetative form, there are a number of significant differences. In particular, the trophozoites of the Vahlkamphiidae family do not have a flagellate stage, whereas *Willaertia* does. Finally, and significantly, in contrast to members of the *Naegleria* genus, *Willaertia* such as *Willaertia magna* C2c Maky is non-pathogenic and non-toxic.

All forms of *Willaertia* amoeba are suitable for therapeutic use in various embodiments of the invention. As amoebae grow they divide in two (e.g., approximately every three hours) so large numbers of amoebae can soon be present should sufficient nutrients be available in the environment. Each individual amoeba surrounds a bacterium (or other microorganism) with its pesudopods, encases it in a food vacuole, and extracts the needed nutrients. Thus, amoebae can be viewed as professional phagocytes that are similar to macrophages and neutrophils (Chen et al., Science, 317:678-68 (2007)). Mechanistically, both amoebae and the immune cells capture bacteria by phagocytosis within cytoplasmic vesicles. These vesicles fuse with lysosomes as a step in the killing of entrapped bacteria.

In some embodiments, amoebae of the species *Willaertia magna* are administered to the subject. These amoebae range in size from 45 to 100 μm in the vegetative form and from 18 to 25 μm in the cyst form, and divide by pro-mitosis. Examples of amoeba strains belonging to the species *Willaertia magna* have been deposited with the ATCC (American Type Culture Collection) and registered under numbers No PTA-7824 and No PTA-7825. These strains belong to the Vahlkampfiidae family. They are characterized by expression of lobular, rounded pseudopods, discharged suddenly when the amoebae move.

While most free-living amoeba are permissive to bacterial contamination, *Willaertia* amoebae behave very differently, targeting many different organisms through phagocytosis. *Willaertia* amoebae have an advantage over soil-based amoeba products for treatment of infection. Soil based amoebas prefer cooler temperatures ~20° Celsius and typically do poorly at warmer temperatures such as those found systemically or on a skin wound. *Willaertia magna* is a warm-water amoeba and prefers temperatures in the 30-45° C. range, which is similar to the temperature of the human body and extremities.

The amoebae used in various aspects of the invention are preferable purified. As used herein, the terms "purified" or "to purify" refer, to the removal of undesired components from a sample. As used herein, the term "substantially purified" refers to amoebae that are at least 60% free, preferably 75% free, and most preferably 90%, or more, free from other components with which they usually associated.

The invention provides a method of treating or preventing a microbial infection in a subject. The infection can be the result of infection by any microorganism. The amoebae have broad-band effects and can be used to treat infection by a variety of different microorganisms. As used herein, the term "infection" is means to include infection caused by a variety of different microorganisms, such as bacteria, archea, fungi, protozoans, *mycoplasma*, and parasitic organisms. Typically, the microorganisms are pathogenic microorganisms.

In some embodiments, the infection is a bacterial infection. Testing by Amoéba Biocide™ (Chassieu, France) has shown that *Willaertia magna* amoebae are effective against a wide variety of bacteria. Specific examples of bacteria include *Staphylococcus aureus* (methicillin-susceptible and -resistant strains; vancomycin-susceptible and -resistant strains), *Streptococcus pyogenes*, *Streptococcus agalactiae*, *Streptococcus anginosus* grp. (including *S. anginosus*, *S. intermedius*, and *S. constellatus*), *Streptococcus dysgalactiae* (including *S. dysgalactiae* subsp. *equisimilis*), *Streptococcus pneumoniae*, Streptococci species, including Streptococci Group A species, Streptococci Group B species, Streptococci Group C species, and Streptococci Group D species, Enterococci species, *Enterococcus faecalis* (vancomycin-susceptible and -resistant strains), *Enterococcus faecium* (vancomycin-susceptible and -resistant strains), *Staphylococcus epidermidis* (methicillin-susceptible and -resistant strains), *Staphylococcus haemolyticus*, all strains, species and subspecies of *Clostridium difficile*, *Acinetobacter baumanii*, *Bacillus anthracis*, *Escherichia coli* (e.g., O157:H7 and K88), *Clostridium botulinum*, *Mycobacterium tuberculosis*, *Legionella pneumophila*, *Listeria monocyto-*

*genes, kiebsella pneumonia, Aeromonas hydrophila, myroides odoratus. Pseudomonas aeruginosa, Shigella sonnei,* and *Salmonella enterica.*

The bacteria may be dormant bacteria, such as one or more of: (i) slow growing bacteria, (ii) stationary-phase bacteria and (iii) bacteria in biofilm form. In other embodiments, the bacteria are antibiotic-resistant or multidrug resistant. Antibiotic resistant bacteria are bacteria shown to be resistant to at least one antibiotic, while multidrug resistant bacteria are bacteria that are resistant to more than one antibiotic. Drug resistant bacteria of particular importance include methycillin resistant *Staphylococcus aureus* (MRSA) and multidrug resistant *Acinetobacter baumannii.*

In some embodiments, the amoebae are administered in cyst form. *Willaertia* cysts are rounded, oval in form or sometimes extremely deformed and have 7 to 12 pores in their wall. When a few cysts are exposed to an aqueous environment, they split open within a few hours and an amoeba emerges from each cyst that immediately begins to feed on the surrounding microorganisms.

The amoebas may be administered to a subject in a number of ways depending upon whether local or systemic treatment is desired and upon the area to be treated. Amoebae in cyst form are more robust and can be used in a variety of different formulations, although amoebae in non-cyst form can be used in some liquid formulations. Pharmaceutically acceptable carriers suitable for administering amoebae include, but are not limited to, solutions, emulsions, and liposome-containing formulations. These compositions may be generated from a variety of components that include, but are not limited to, preformed liquids, self-emulsifying solids and self-emulsifying semisolids.

Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration (e.g., to tissues, wounds, organs, etc) may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The amoebas used in accordance with the invention have the advantage that they are compatible with a host of pharmaceutical agents and do not adversely affect their effectiveness. In some embodiments, the method further comprises co-administering a therapeutic agent to the subject. Agents which treat or prevent infection or promote wound healing are preferably used. As used herein, the term "co-administration" refers to the administration of a therapeutic agent in addition to administration of amoebas to a subject. In some embodiments, the co-administration of the therapeutic agent and the amoebas is concurrent. In some embodiments, the therapeutic agent is administered before or after administration of amoebaes. Those of skill in the art understand that the formulations and/or routes of administration of the various agents/therapies used may vary. The appropriate dosage for co-administration can be readily determined by one skilled in the art. In some embodiments, when amoebae and a therapeutic agent are co-administered, they can be administered at lower dosages than appropriate for their administration alone. Thus, co-administration is especially desirable in embodiments where the co-administration of the agents/therapies lowers the requisite dosage of a known potentially harmful (e.g., toxic) agent(s).

In some embodiments, the amoebae are administered in combination with known antimicrobial agents. There are an enormous amount of antimicrobial agents currently available for use in treating bacterial and fungal. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); and antimetabolites (e.g., trimethoprim and sulfonamides). Various combinations of antimicrobials may be employed.

Antimicrobial agents may be selected from the group consisting of antiseptics and antibiotics and mixtures thereof. Suitable antibiotics include peptide antimicrobials (e.g. defensins, Magainin, synthetic derivatives of them) tetracycline, penicillins, terramycins, erythromycin, bacitracin, neomycin, polymycin B, mupirocin, clindamycin and mixtures thereof. Suitable antiseptics include silver sulfadiazine, chiorhexidine, povidone iodine, triclosan, other silver salts and colloidal silver, sucralfate, quaternary ammonium salts and mixtures thereof.

Pain relieving agents may be selected from the group consisting of an anaesthetic, an analgesic, an antiinflammatory or mixtures thereof. Suitable anesthetics include lidocaine or novocaine. Suitable analgesics include non-steroidal anti-inflammatory drugs (NSAIDs). Suitable antiinflammatory agents include steroids such as prostaglandins.

Growth factors may be selected from the group consisting of platelet derived growth factor (PDGF), fibroblast growth factor (FGF), transforming growth factor beta (TGF-β), epidermal growth factor (EGF), vascular endothelial growth factor (VEGF) and insulin-like growth factor (IGF), and mixtures thereof.

Treatment of Skin Wounds

In some embodiments, the subject has a skin wound, and the amoebas are administered to the skin wound. Accordingly, in this embodiment, the invention provides a method of treating or preventing infection of a skin wound in a subject by administering a therapeutically effective amount of amoebas of the genus *Willaertia* in a pharmaceutically acceptable carrier to the skin wound of the subject. In some embodiments, the amoebas used are of the *Willaertia magna* species, while in further embodiments, the amoebas used are in their cyst form.

As used herein, the term "wound" refers to a disruption of the normal continuity of structures caused by a physical (e.g., mechanical) force, a biological (e.g., thermic or actinic force, or a chemical means. In particular, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, and biting, and other types of wounds. Examples of skin wounds include lacerations, abrasions, surgical incisions, chronic wounds, pressure ulcers, venous ulcers, or skin burns.

In some embodiments, the skin wound being treated is a chronic wound. As used herein, the term "chronic wound" refers to a wound that does not fully heal even after a prolonged period of time (e.g., 2 to 3 months or longer). The treatment of chronic infections of the skin often is a challenge to clinicians. Infected, burns, surgical wounds, and diabetic lesions can be refractory to current treatment regimes causing them to persist as open sores. The most common underlying reasons for this type of pathology are: antibiotic failure due to high bacterial loads, infection with multiple antibiotic-resistant pathogens, or the formation of antibiotic-impervious biofilms. Chronic wounds often occur in patents having impaired wound healing Impaired wound healing can be a result of a variety of conditions, such as infection of the wound, the patient being diabetic, or the patient being elderly.

In some embodiments, the skin wound being treated is a pressure sore. Pressure sores are also known as bedsores or pressure ulcers. Pressure sores are injuries to skin and underlying tissue resulting from prolonged pressure on the skin. Pressure sores most often develop on skin that covers bony areas of the body, such as the heels, ankles, hips and tailbone.

In some embodiments, the wound being treated is an ulcer. As used herein, the term "ulcer" (i.e., "ulceration") refers to a local defect or excavation of the surface of an organ or tissue, produced by sloughing of necrotic tissue. The term encompasses various forms of ulcers (e.g., diabetic, neuropathic, arterial, decubitus, dental, perforating, phagedenic, rodent, trophic, tropical, varicose, venereal, etc.), although in preferred embodiments, surface (i.e., skin) ulcers are involved in the present invention.

In some embodiments, the method further includes placing a wound dressing onto the skin wound of the subject. Suitable wound dressings are described further herein. The amoebae can be administered separately, before placement (or re-placement) of a wound dressing, or in some embodiments the amoebae can be included in the wound dressing, and subsequently administered from the wound dressing to the skin wound.

In some embodiments, the method further comprises contacting the wound with collagen. Contacting, as used herein, refers to causing two items to become physically adjacent and in contact, or placing them in an environment where such contact will occur within a reasonably short timeframe. For example, contacting a skin wound with collagen includes placing the collagen at or near a skin wound such that the collagen will interact with the skin wound to stimulate wound healing and/or other beneficial effects.

In some embodiments, amoebae (e.g., *Willaertia* cysts) are incorporated into bandages, dressings, or other wound coverings. In addition, in some embodiments, spores are incorporated into salves, ointments, or other topical applications. Pharmaceutical compositions and formulations for topical administration (e.g., to tissues, wounds, organs, etc) may include transdermal patches, ointments, lotions, creams, gels, drops, suppositories, sprays, liquids and powders. Conventional pharmaceutical carriers, aqueous, powder or oily bases, thickeners and the like may be necessary or desirable.

In some embodiments, amoebae are delivered in a pharmaceutically acceptable carrier. A pharmaceutically acceptable carrier refers to any of the standard pharmaceutical carriers including, but not limited to, saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For example, of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be inoculated for horticultural or agricultural use. Such formulations include dips, sprays, seed dressings, stem injections, sprays, and mists.

Medical Systems

In another aspect, the present invention provides a system, comprising a composition including one or more species of amoeba of the genus *Willaertia*; and a medical device comprising said composition. Medical devices include any material or device that is used on, in, or through a subject's or patient's body, for example, in the course of medical treatment (e.g., for a disease or injury). Medical devices include, but are not limited to, such items as medical implants, wound care devices, drug delivery devices, birth control and body cavity and personal protection devices. Examples of medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incision drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, intrauterine devices (IUDs), diaphragms, and condoms.

The composition comprising the one or more species of amoeba of the genus *Willaertia* can include any suitable pharmaceutically acceptable carrier or pharmaceutically acceptable support material. In some embodiments, the amoebas included in the composition are of the *Willaertia magna* species. In other embodiments, the amoebas are in the cyst form.

The medical device can include a variety of different biocompatible materials, including but not limited to silicon, plastic, glass, polymer, ceramic, skin, tissue, nitrocellulose, hydrogel, paper, polypropylene, cloth, cotton, wool, wood, brick, leather, vinyl, polystyrene, nylon, polyacrylamide, optical fiber, natural fibers, nylon, metal, rubber, soil and composites thereof.

In some embodiments, the medical device comprises an antibiotic wound dressing. Antibiotic wound dressings include a sterile pad or compress applied to a wound to promote healing and protect the wound from further harm. Dressings are designed to be in direct contact with the wound. Examples of wound dressings include low adherent dressings, semipermeable films, hydrocolloids, hydrogels, alginates, and foam dressings. The presence of amoebae within the wound dressing results in the wound dressings having an antibiotic effect. For a review of suitable wound dressings, see Jones et al., "Wound dressings," BMJ, 332 (7544): 777-780 (2006).

The preparation of the tissue prior to placement of an antibiotic wound dressing can take place in the conventional manner. Wounds are preferably debrided beforehand and thoroughly washed, the use of PHMB-containing wound flushing solutions, such as Prontosan™ being especially recommended. The wound dressing of the invention can remain for 72 hours or longer on the wound due to the high absorption resistance. Since the infection risk is minimal and the wound dressing gels over time and is almost completely decomposed to short-chain peptides, it is not necessary at all to remove the old wound dressing from the wound. Rather another wound dressing in accordance with the invention can be applied to/over the old one. If the old wound dressing is to be removed, this can, if necessary, take place using PHMB-containing or other suitable wound flushing solution. Then, the wound is preferably cleaned again with the wound flushing solution before the new wound dressing is applied.

The wound dressing materials according to the present invention may be provided in the form of beads, flakes, powder, and preferably in the form of a film, a fibrous pad, a web, a woven or non-woven fabric, a freeze-dried sponge, a foam or combinations thereof. In certain embodiments, the polymer is selected from the group consisting of. In other embodiments, the material may comprise (or consist essentially of) a freeze-dried sponge or a solvent-dried sponge.

Antibiotic wound dressings are suitable for use in a range of medical applications, including the treatment of acute surgical and traumatic wounds, burns, fistulas, venous ulcers, arterial ulcers, pressure sores (otherwise known as decubitus ulcers), diabetic ulcers, ulcers of mixed aetiology, and other chronic or necrotic wounds and inflammatory lesions and disorders.

Figure 2:
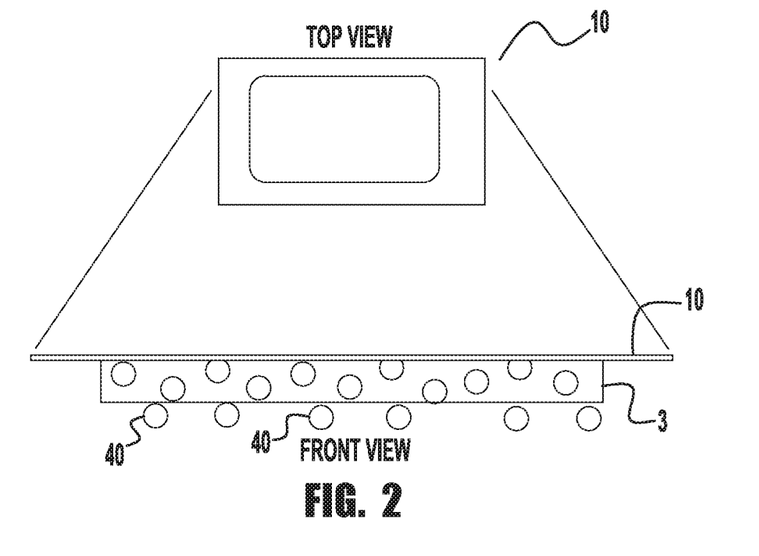
FIG. 2 provides a figure showing an antibiotic wound dressing.

In some embodiments, the present invention provides an antibiotic wound dressing 10 comprising a backing 20 having a first surface and a second surface opposite the first surface; a pharmaceutically acceptable support material 30 applied to a portion of the first surface of the backing; and one or more amoebas 40 of the genus *Willaertia* dispersed within the pharmaceutically acceptable support material. An antibiotic wound dressing 10 is shown in FIG. 2.

The antibiotic wound dressing comprises a backing 20. The backing is typically a sheet having a first surface and a second surface opposite the first surface, extending over the pharmaceutically acceptable support material opposite to the wound facing side. The backing sheet may be larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

The backing may be water-permeable or water-impermeable. When the backing is water-impermeable, the resulting adhesive dressings are suitable as wet dressings. When the antibiotic wound dressing is designed for occlusive dressings or wet dressings, the backing is water-impermeable material such as silicone or polyurethane. In some embodiments, the backing sheet is semipermeable. That is to say, the backing sheet is preferably permeable to water vapor, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 $g/m^2/24$ hrs, preferably 500 to 2000 $g/m^2/24$ hrs at 37.5° C. at 100% to 10% relative humidity difference. It has been found that such moisture vapor transmission rates allow the wound under the dressing to heal under moist conditions without causing the skin surrounding the wound to macerate.

In other embodiments, the backing is made of biocompatible absorbent or water-permeable materials. Materials of the backing are not specifically limited as long as the above-mentioned requirements are satisfied. However, fabric (woven fabrics, knitted fabrics, and nonwoven fabrics) or paper may suitably be used.

The backing may be made of one, two or more of various materials. Examples include resins and rubbers such as, but not limited to, silicone, tetron, acrylics, cellophane, fluorocarbon resins, ionomers, nylon, polycarbonate, polyester, polyethylene, polypropylene, polystyrene, polyurethane, polyvinyl alcohol, polyvinylidene chloride, polyvinyl chloride, vinyl acetate, rubber chloride, and vinyl chloride. The backing may be subjected to secondary processing such as coating and corona treatment.

In some embodiments, the backing is a transparent. Transparent backings improve the ability to easily inspect the wound and evaluate the progress of wound healing. The transparency should be such that wound is visible when the antibiotic wound dressing is positioned over the wound of a subject.

In some embodiments, the antibiotic wound dressing further comprises an adhesive layer provided on at least a part of the first surface of the backing to secure the adhesive dressing to the skin and over the wound of a subject. The adhesive for the adhesive layer may be any one of appropriate adhesives that can hold the backing on the surface of the skin of a wearer for a relatively long period of time. The adhesive may be selected from a range of adhesives that do not have adverse effects on the skin. The adhesive may be, for example, "SK dyne MD-1" available from the Soken Chemical & Engineering Co., Ltd., Tokyo, Japan.

The antibiotic wound dressing also includes a pharmaceutically acceptable support material applied to a portion of the first surface of the backing. The pharmaceutically acceptable support material is a pharmaceutically acceptable carrier for the amoebas that can be deposited on the backing of the antibiotic wound dressing. The term pharmaceutically acceptable support material refers to materials or compositions that are not only compatible with the amoebae and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable support materials suitable for use in the present invention include collagen, cellulose, chitosan or hyaluronic acid containing bandages, gauze, resorbable hydrogels or polymers such as PEG, polycaprolactone, LPGA, gelatin, glycerin, clay composed dressing, etc. Examples of pharmaceutically acceptable support materials also include decellularized extracellular matrix materials such as decellularized peritoneal membrane (See Barnes et al., Biomaterials, 32(1):137-43 (2011)), and collagen.

In some embodiments, the pharmaceutically acceptable support material comprises collagen. Collagen as the albuminoid protein of the connective tissue is a component of the bodies of mammals. Collagen is ordinarily obtained from the tendons and/or skins of cattle, swine or horses. Depending on its origin and its structure, collagen is divided into different types. All types of collagen share a triple helix structure which is formed from three polypeptide chains. Collagen has the advantage compared to other materials that it acts hemostatically. Therefore, one application of collagen lies in dressing of wounds, especially those wounds in which some of the dermal structures or also the structures which lie under the skin have been involved. Collagen is used to treat both acute and chronic wounds.

Collagen can be used in all of the aspects of the invention described herein. For example, collagen can be included when amoebae are administered to a wound, either in a pharmaceutically acceptable carrier or as part of an antibiotic wound dressing. Depending on the type of use planned, the origin, type and preparation form of the collagen can be chosen in the conventional manner. Production takes place, basically, in the manner described in the prior art from animal starting material, for example, from the tendons and/or skin of cattle, swine or horses, equine collagen being preferred. The type of collagen used is likewise not especially limited, but types I, III and X can be used.

The preparation form of the collagen likewise corresponds to that which is already known from the prior art. For example, the collagen can be present in the form of a porous sponge, a foil, a film, a membrane, a nonwoven or a tamponade. All these preparation forms can be produced in the manner which is conventional in the prior art. Before use, the collagen material is preferably sterilized in the known manner. Sterilization with ethylene oxide or gamma radiation, preferably with 28 kGray±10%, is especially suitable for this purpose. The size of the preparation forms depends on the intended use. Conventionally, the collagen material will have a thickness between 0.1 and 20 mm, and preferably, between 2 and 7 mm.

The wound facing surface of the dressing is preferably protected before use by a removable cover sheet. The cover sheet is normally formed from flexible thermoplastic material. Suitable materials include polyesters and polyolefins. Preferably, the adhesive-facing surface of the cover sheet is a release surface. That is to say, a surface that is only weakly adherent to the active layer and the adhesive on the backing sheet to assist peeling of the adhesive layer from the cover sheet. For example, the cover sheet may be formed from a non-adherent plastic such as a fluoropolymer, or it may be provided with a release coating such as a silicone or fluoropolymer release coating.

Figure 3:
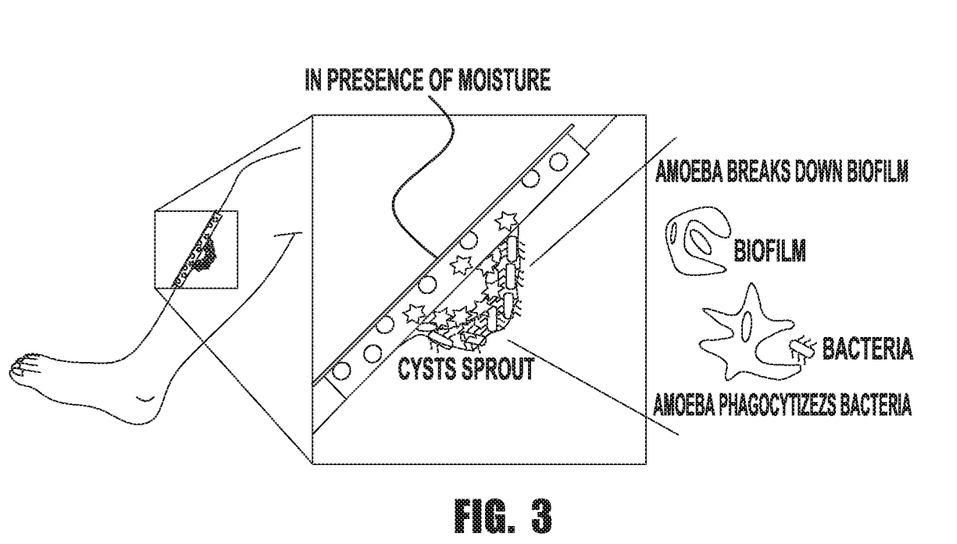
FIG. 3 provides a scheme showing how amoeba cysts of an antibiotic wound dressing sprout in the presence of moisture and proceed to attack bacteria and biofilm.

FIG. 3 provides a scheme showing the use of an antibiotic wound dressing of the present invention for treatment of a skin wound. In this embodiment, *Willaertia* cysts are included in the pharmaceutically acceptable support material of the dressing. In the presence of moisture, such as that provided by contact with a skin wound, the cysts sprout to form amoebas which enter the wound where they break down any biofilm that may be present and phagocytize any microorganisms (e.g., bacteria) that may have infected the wound.

Wound Treatment Kits

Figure 4:
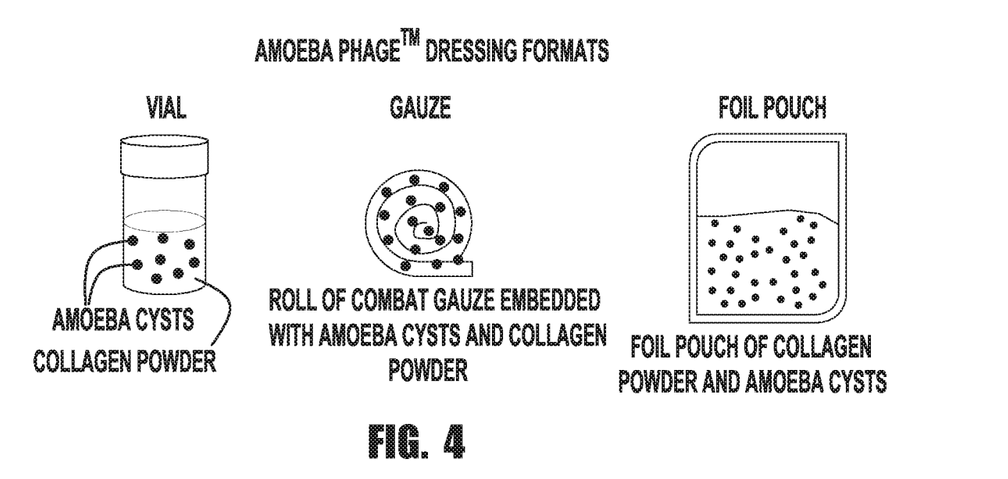
FIG. 4 provides a figure showing various different wound treatment kits including a therapeutically effective amount of *Willaertia* amoebae, including collagen powder in a vial, a roll of gauze including collagen powder, and a collagen-containing pouch.

Another aspect of the invention provides a wound treatment kit. The wound treatment kit includes a therapeutically effective amount of amoebas of the genus *Willaertia* in a pharmaceutically acceptable carrier; and a package for holding the pharmaceutically acceptable carrier including the amoebas. Examples of wound treatment kits for providing therapeutically effective amounts of amoebas to subjects are shown in FIG. 4. In some embodiments, the kit includes a plurality of different species of *Willaertia* amoebae. In further embodiments, the amoebas are of the *Willaertia magna* species.

In some embodiments, amoebae are in the cyst form that is stable for long term storage. In other embodiments, amoebae are stored and transported in different stages. In some embodiments, the pharmaceutically acceptable carrier or storage material comprises additional components (e.g., storage reagents, buffers, preservatives, stabilizers, etc.). Another method of long-term storage of cysts is lyophilization. In other embodiments, amoebae or cysts are stored short-term at 4° C. in agar.

Suitable packages include, for example, bottles, vials, pouches (e.g., a foil pouch), or syringes. The package may be formed from a variety of materials such as glass or plastic. The package holds an amoeba-containing composition that may be effective for treating infection and may have a sterile access port (e.g., the container may be an intravenous solution bag or a vial having a stopper pierceable by a hypodermic injection needle). A label or package insert included with the kit may indicate that the composition may be used for treating the condition of choice, such as a skin wound. Preferably, the kit is sterile and is packaged in a microorganism-impermeable container.

The kit may also include other materials useful for treating infection. For example, the kit can include wound dressing material such as gauze, bandages, and adhesive. In some embodiments, the kit includes an antibiotic wound dressing as described herein. In some embodiments, the kit further includes collagen, which can serve as a pharmaceutically acceptable carrier or support material for the amoebas. In some embodiments, the collagen comprises powdered collagen. The kit can also include one or more therapeutic agents that can be co-adminstered with the amoebas.

In some embodiments, the kit further includes instructions for using the kit to carry out a method of treating or preventing infection in a subject by administering to the subject a therapeutically effective amount of *Willaertia* amoebas. For example, in some embodiments, the kit includes instructions for carrying out a method of providing an antibiotic wound dressing including *Willaertia* amoebas to a subject. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The following example is included for purposes of illustration and is not intended to limit the scope of the invention.

EXAMPLE

In Vitro Testing of *Willaertia magna* Amoeba Against Clinical Multi-Drug Resistant Isolates of *Staphylococcus aureus* and *Acinetobacter baumanii*

Methods

*Willaertia magna* amoebas were cultured in T175 suspension culture flasks such that the amoeba grew in an exponential fashion and were in the feeding trophozoite form. *Willaertia magna* amoeba were subsequently applied at exponentially increasing levels of multiplicity of infection (MOI) to a co-culture of *Staphylococcus aureus* (SA) or *Acinetobacter baumanii* (AB) in distilled water. Co-cultures were incubated for 24 hours and bacterial colony forming units (CFUs) were subsequently counted. SA was inoculated onto a tissue culture plate and incubated to allow a bacterial lawn to develop. Subsequently, a pipette was used to obtain a sample of *Willaertia magna* amoeba at different concentrations (e.g., $10^x$ Amoeba, where x is labeled on the culture plate) and then a single drop (e.g., 10 µL) was placed onto the lawn. The lawn was allowed to sit and the tissue culture plates were subsequently inspected to determine the presence of a zone of inhibition, if any.

Results

Figure 5A:
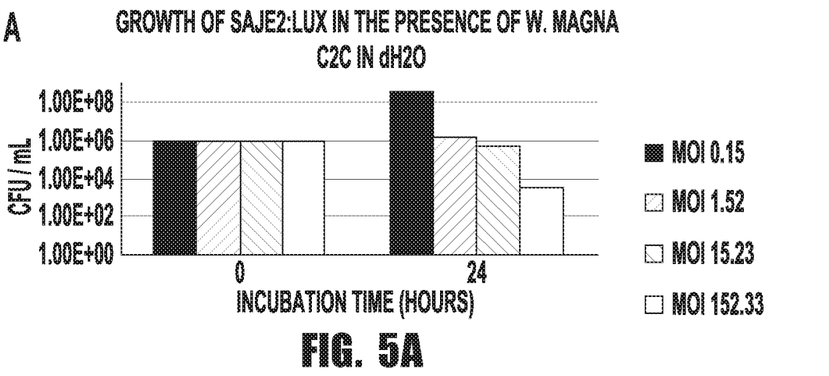
FIGS. 5A-C provides graphs (A,B) showing the results of in vitro tests demonstrating that *Willaertia magna* is effective against MDR *Staphylococcus aureus*, but not *Acinetobacter baumanii*, and (C) an image showing *Willaertia magna* applied to a plaque of *Staphylococcus aureus* creates a zone of inhibition.
Figure 5B:
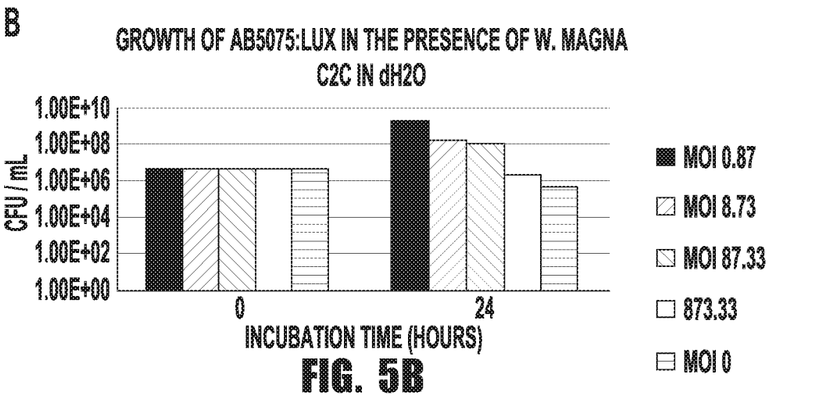
Figure 5C:
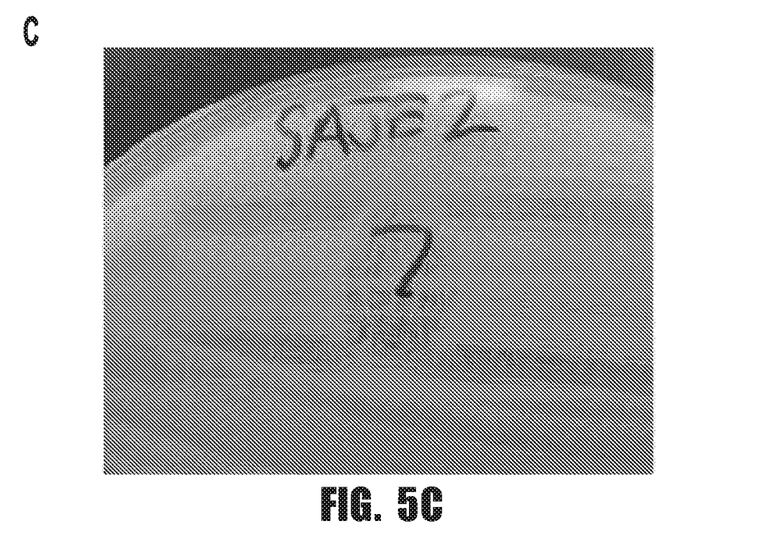

The *Willaertia magna* showed a 2-log reduction in SA, with larger MOIs showing a greater reduction. A similar but less substantial decreased was shown in AB. At lower MOIs, the bacteria appear to have overrun the amoebas and the CFUs increased. *Willaertia magna* showed a zone of inhibition on SA at concentrations of $10^7$ amoeba. The results are shown in FIG. 5.

Discussion

The *Willaertia magna* amoebae were able to reduce the presence of SA in both co-culture as well as on bacterial lawn spot plates. *Willaertia magna* was marginally effective against AB in both co-culture and bacterial lawn spot plates. Why the *Willaertia magna* appears to be more effective against SA than AB is unknown; however, it may be because SA is a gram-positive bacteria while AB is gram-negative. In general, gram negative bacteria have a thin protective outer covering which can make it more difficult to fight these bacteria. The reduced efficacy against AB may also be due to the increased virulent nature of the MDR clinical bacterial isolates used in the study.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds of the invention are effective, the inventors are not bound by theories described herein. The invention is not limited to the exact details shown and described, for variations obvious to one skilled in the art will be included within the invention defined by the claims.

What is claimed is:

1. A method of treating or preventing a microbial infection in a subject, comprising: contacting a microorganism within the subject with a composition comprising one or more species of amoebae of the genus *Willaertia*.

2. The method of claim 1, wherein the composition comprises one or more species of amoebae of the genus *Willaertia* in a pharmaceutically acceptable carrier.

3. The method of claim 1, wherein the subject has a skin wound, and the amoebas are administered to the skin wound.

4. The method of claim 3, wherein the skin wound is a chronic wound.

5. The method of claim 3, further comprising placing a wound dressing onto the skin wound of the subject.

6. The method of claim 1, wherein the one or more species of amoebae is a *Willaertia magna* species of amoebas.

7. The method of claim 1, wherein the microbial infection is a bacterial infection.

8. The method of claim 7, wherein the bacteria are antibiotic-resistant.

9. The method of claim 7, wherein the amoebas are administered from the wound dressing.

10. The method of claim 1, wherein the amoebas are administered in cyst form.

11. The method of claim 1, further comprising contacting the wound with collagen.

12. The method of claim 1, further comprising co-administering a therapeutic agent to the subject.

* * * * *

UNITED STATES PATENT AND TRADEMARK OFFICE
CERTIFICATE OF CORRECTION

| | |
|---|---|
| PATENT NO. | : 11,202,806 B2 |
| APPLICATION NO. | : 16/342617 |
| DATED | : December 21, 2021 |
| INVENTOR(S) | : Justin J. Baker et al. |

It is certified that error appears in the above-identified patent and that said Letters Patent is hereby corrected as shown below:

In the Specification

Column 1, before the subtitle BACKGROUND insert the following paragraph:
--GOVERNMENT FUNDING
This invention was made with government support under PR170442 awarded by United States Army Medical Research Acquisition Activity. The government has certain rights in the invention.--

Signed and Sealed this
Thirteenth Day of December, 2022

Katherine Kelly Vidal
*Director of the United States Patent and Trademark Office*